United States Patent
Guillard

(10) Patent No.: US 10,703,683 B2
(45) Date of Patent: Jul. 7, 2020

(54) FACILITY FOR TREATING AND RECYCLING ANIMAL WASTE COMPRISING METHANISATION, CULTIVATION OF MICROALGAE AND MACROPHYTES, AND VERMICULTURE

(71) Applicants: René-Jean Guillard, Dongguan, Guangdong Province de (CN); Skyworld International Overseas Limited, Hong Kong (CN)

(72) Inventor: René-Jean Guillard, Dongguan (CN)

(73) Assignee: SKYWORLD INTERNATIONAL OVERSEAS LIMITED, Central Hong Kong (CN)

( * ) Notice: Subject to any disclaimer, the term of this patent is extended or adjusted under 35 U.S.C. 154(b) by 665 days.

(21) Appl. No.: 14/900,908

(22) PCT Filed: Jun. 30, 2014

(86) PCT No.: PCT/IB2014/001234
§ 371 (c)(1),
(2) Date: Jun. 2, 2016

(87) PCT Pub. No.: WO2014/207547
PCT Pub. Date: Dec. 31, 2014

(65) Prior Publication Data
US 2016/0264484 A1    Sep. 15, 2016

(30) Foreign Application Priority Data

Jun. 28, 2013   (FR) ..................................... 13 01538

(51) Int. Cl.
*C05F 3/06*    (2006.01)
*C12M 1/00*    (2006.01)
(Continued)

(52) U.S. Cl.
CPC ................. *C05F 3/06* (2013.01); *A01G 7/02* (2013.01); *A01G 9/14* (2013.01); *A01G 17/00* (2013.01);
(Continued)

(58) Field of Classification Search
CPC .... C05F 3/06; C05F 17/0009; C05F 17/0027; C05F 17/0288; A01G 22/00; A01G 7/02;
(Continued)

(56) References Cited

U.S. PATENT DOCUMENTS 5,078,882 A  *  1/1992  Northrop ................ C02F 3/02
                                                        210/602
2008/0050800 A1    2/2008  McKeeman et al.
(Continued)

FOREIGN PATENT DOCUMENTS

GB            2484530 A  *  4/2012  ............. A01G 33/00

OTHER PUBLICATIONS

Malik et al, "Environmental challenge vis a vis opportunity: The case of water hyacinth"; Environment international, Pergamon Press, vol. 33, No. 1, Dec. 2006, pp. 122-138 (Year: 2006).*
(Continued)

*Primary Examiner* — William H. Beisner
*Assistant Examiner* — Danielle B Henkel
(74) *Attorney, Agent, or Firm* — Pearne & Gordon LLP

(57) ABSTRACT

A facility for treating and recycling animal waste (2), including a unit (6) for methanizing the waste including treatment of the obtained biogases, a cogeneration unit (8) delivering electricity and heat (32) from the biogases, and a unit for hydroponically cultivating microalgae (14) in photobioreactors supplied by the liquid phase (12) of the organic residues from the methanization. The facility further includes a unit for cultivating macrophytes (22) supplied with water (20) leaving the unit for cultivating microalgae,
(Continued)

and a vermiculture unit (24) fed by harvesting the macrophytes (22) and by the sludge (36) coming from the raw digestate from the methanization.

16 Claims, 2 Drawing Sheets

(51) Int. Cl.

| | |
|---|---|
| *C02F 11/04* | (2006.01) |
| *C12M 1/107* | (2006.01) |
| *C02F 3/32* | (2006.01) |
| *C02F 9/00* | (2006.01) |
| *A01G 22/00* | (2018.01) |
| *C05F 17/05* | (2020.01) |
| *C05F 17/50* | (2020.01) |
| *C05F 17/90* | (2020.01) |
| *A01G 7/02* | (2006.01) |
| *A01G 9/14* | (2006.01) |
| *A01G 17/00* | (2006.01) |
| *A01G 31/02* | (2006.01) |
| *A01G 33/00* | (2006.01) |
| *C02F 103/20* | (2006.01) |
| *C02F 3/28* | (2006.01) |

(52) U.S. Cl.
CPC ............ *A01G 22/00* (2018.02); *A01G 31/02* (2013.01); *A01G 33/00* (2013.01); *C02F 3/32* (2013.01); *C02F 3/322* (2013.01); *C02F 9/00* (2013.01); *C02F 11/04* (2013.01); *C05F 17/05* (2020.01); *C05F 17/50* (2020.01); *C05F 17/989* (2020.01); *C12M 21/02* (2013.01); *C12M 21/04* (2013.01); *C12M 43/06* (2013.01); *C12M 43/08* (2013.01); *C02F 3/28* (2013.01); *C02F 3/327* (2013.01); *C02F 2103/20* (2013.01); *C02F 2303/10* (2013.01); *Y02A 40/208* (2018.01); *Y02E 50/343* (2013.01); *Y02P 20/145* (2015.11); *Y02W 10/18* (2015.05); *Y02W 10/23* (2015.05); *Y02W 10/30* (2015.05); *Y02W 10/37* (2015.05); *Y02W 30/43* (2015.05); *Y02W 30/47* (2015.05)

(58) Field of Classification Search
CPC .......... A01G 9/14; A01G 17/00; A01G 31/02; A01G 33/00; C02F 3/32; C02F 3/322; C02F 9/00; C02F 11/04; C02F 3/28; C02F 3/327; C02F 2103/20; C02F 2303/10; C12M 21/02; C12M 21/04; C12M 43/06; C12M 43/08; Y02W 10/18; Y02W 10/23; Y02W 10/30; Y02W 10/37; Y02W 30/43; Y02W 30/47; Y02P 20/145; Y02A 40/208; Y02E 50/343
See application file for complete search history.

(56) References Cited

U.S. PATENT DOCUMENTS

| | | | |
|---|---|---|---|
| 2009/0250393 A1* | 10/2009 | Williams | C02F 3/28 210/602 |
| 2009/0294354 A1 | 12/2009 | Theodore et al. | |
| 2010/0105127 A1* | 4/2010 | Ginsburg | C02F 11/04 435/262 |
| 2015/0118723 A1* | 4/2015 | Duzoglou | C12M 43/00 435/134 |
| 2019/0078049 A1* | 3/2019 | Smith | C12M 41/48 |

OTHER PUBLICATIONS

International Search Report for PCT/IB2014/001234 dated Nov. 10, 2014.
Written Opinion for PCT/IB2014/001234 dated Nov. 10, 2014.
Chongrak Polprasert, et al.: "Productive Utilization of Pig Farm Wastes: A Case Study for Developing Countries", Resources Conservation and Recycling, Jun. 30, 1994, pp. 245-259, vol. 11, No. 1/04, Elsevier Science Publisher, Amsterdam, NL, XP000453896.

* cited by examiner

FACILITY FOR TREATING AND RECYCLING ANIMAL WASTE COMPRISING METHANISATION, CULTIVATION OF MICROALGAE AND MACROPHYTES, AND VERMICULTURE

TECHNICAL FIELD OF THE INVENTION

The present invention relates to a facility for treating and recycling animal waste, as well as a method for treating and recycling these effluents.

The management of livestock effluents, especially liquid manure from pig farms, is one of the major problems of this activity for years to come, especially with the environmental problems that they create and the regulations that have been put in place.

TECHNICAL BACKGROUND OF THE INVENTION

Effluents from animal farms such as pig slurry, rich in the nutrient elements nitrogen, phosphorus and potassium "NPK", are usually applied to agricultural land as fertilizer following spreading plans controlled by regulations. To limit pollution of soils, water basins and aquifers, authorized application rates are increasingly reduced.

This spreading can also achieve a concentration of said NPK elements on some seashores, which, with the heat, cause the proliferation of green algae, which are difficult to reuse because of their sea salt and sand loads.

Another use of these effluents is their treatment in dedicated dehydration facilities to obtain extracts concentrated in NPK elements, allowing delivery to external customers. However, these treatments require energy input and produce different materials that are not all used locally. The ecological balance may be poor, and the costs are not optimized.

A known process for treating animal waste, presented notably by document GB-A-2484530, achieves methanization of these effluents, producing mainly methane, carbon dioxide and heat. The materials derived from this methanization fuel a culture of microalgae to obtain upgraded products.

It is possible in particular to obtain, by means of a cogenerator using the methane, a production of electrical energy consumed on site or fed back into an electricity network, and of heat used for heating buildings or local activities.

Furthermore, another known treatment process, presented notably by document US-A1-2009/0294354, uses the liquid leaving the microalgae culture for feeding a culture of water plants in order to consume the nutritious products from this liquid.

A problem that arises with these methods is that some residual materials produced are not economically recoverable. In addition, these activities do not have a biological balance, and furthermore they do not consume all the main materials produced. It is then necessary to treat the residues that can cause processing, transport or disposal problems, increasing the overall cost of effluent treatment and degrading the ecological balance.

In particular, methanization and the cultivation of water plants produce sludge and a large amount of contaminated water, which must be removed, in particular by discharging the water or by spreading. However, these releases and this spreading may cause pollution of soil or water; they are thus subject to regulations and are increasingly limited.

GENERAL DESCRIPTION OF THE INVENTION

The present invention aims notably to avoid these disadvantages of the prior art. However, its huge advantage is that the sequence of the different steps it advocates, adds value to 100% of the input and yet produces no waste off site.

It proposes to this effect a facility for treating and recycling animal waste, comprising a methanization unit capable of producing and treating the biogas obtained, a cogeneration unit providing electricity and heat from these biogas, a hydroponic unit for cultivating microalgae in photo-bioreactors fed by part of the liquid phase of the raw digestate produced by the methanization, and a system of separation capable of supplying a digestate liquid phase and a solid phase comprising digestate sludge, wherein said installation is characterized in that it further comprises a macrophyte culture unit fed by the water emerging from the microalgae culture unit and by another part of the liquid phase of the raw digestate produced by the methanization, and a vermiculture unit fed by the harvested macrophytes, and by the sludge constituting the solid phase of the raw digestate from methanization.

An advantage of this system is that it is possible to achieve with these different units, grouped in the facility, and with light, or even the sun, a series of transformation processes comprising interactions using a large proportion of the materials as well as the energy generated that is renewable.

It must be noted that each of the processes that are successively implemented by the invention is a natural biological process that can ensure the decontamination of the NPK entering the site.

This combination allows the value of the products obtained to be maximized, which are even fully recovered, limiting transport, reducing the wastewater treatment costs and optimizing the environmental impact. In addition, it has the enormous advantage of producing no waste to be eliminated, and it achieves a capture of carbon dioxide.

In particular, feeding vermiculture with the sludge produced by the methanization unit and with the plants produced by the culture of macrophytes, this sludge is treated and the large amount of water released by installation is absorbed, eliminating release into nature. Furthermore, this vermiculture provides highly valued products of high economic value.

Generally, by adjusting the size of each unit, the different successive processes that occur spontaneously in nature with the natural cycle of life are reproduced to solve the problem of treating effluents.

The treating and recycling facility according to the invention may further comprise one or more of the following features, which can be combined with one another.

Advantageously, the digesters of the methanization unit are pools covered by greenhouses of the microalgae, macrophyte or vermiculture culture units.

Advantageously, the macrophyte culture unit uses a plant of the family *Eichhornia crassipes*.

Advantageously, the macrophytes are grown in greenhouses, above ground in pools heated to about 25° C.

In particular, the culture pools can have a depth of about 30 cm and a width of about 2 m, and form rows separated by a runway for a machine to roll on.

Advantageously, the earthworms of the vermiculture are of the "Californian" type.

Advantageously, the facility comprises a system that keeps the vermiculture compost at a humidity percentage of the medium that is greater than 80%.

Advantageously, the vermiculture unit comprises percolate recovery means.

In particular, the vermiculture compost may be placed in greenhouses directly on the ground on a waterproof tarpaulin, with drains being installed for recovering the percolate.

Advantageously, the vermiculture unit is heated to about 20° C. by a hot water circulation coming from the methanization and cogeneration units.

The facility may further comprise a timber operation enriched by the vermiculture compost.

Advantageously, the timber operation uses willow in short rotation for pruning cycles.

The invention also relates to a method for treating and recycling animal waste comprising the following steps: a methanization of the effluents comprising a processing of the biogas obtained, a cogeneration supplying electricity and heat from these biogas, a hydroponic microalgae culture in photo-bioreactors fed by part of the liquid phase of raw digestate produced by the methanization, a separation supplying a digestate liquid phase and a solid phase comprising digestate sludge, a macrophyte culture fed by the water emerging from the microalgae culture unit and by another part of the liquid phase of the raw digestate produced by the methanization, and a vermiculture fed by the harvested macrophytes, and by the sludge constituting the solid phase of the raw digestate from methanization.

The detailed specifications of the invention are given in the following description in conjunction with the accompanying drawings. It should be noted that these drawings have no other purpose than to illustrate the text of the description and that they thus do not in any way constitute a limitation of the scope of the present invention.

DESCRIPTION OF A PREFERRED EMBODIMENT OF THE INVENTION

Figure 1:
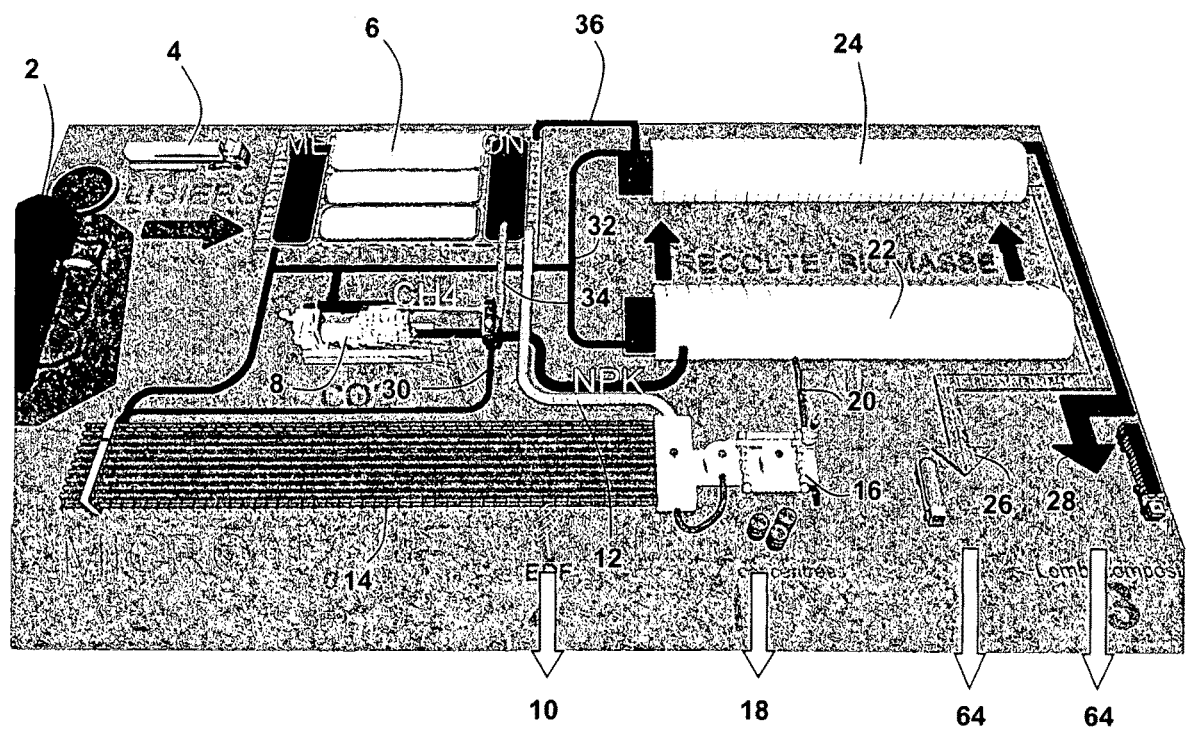
FIG. 1 is a diagram of a facility according to the invention.

FIG. 1 shows schematically a treatment and recycling facility receiving effluent from the farms of the region 2 arriving by means of the transporters 4, wherein said facility comprises for its known part a methanization unit 6 producing biogas 34 supplied to a cogeneration unit 8 producing electricity used on the entire site, with excess production being fed into the external electricity distribution network 10.

The methanization unit 6 produces organic residues rich in NPK nutrients, whose liquid phase 12 feeds a hydroponics microalgae culture unit 14 in a greenhouse of the vegetable crop type in photo-bioreactors. The production of this crop is processed by a concentration and packaging station 16 to obtain concentrated recovery products that can be easily transported, with a reduced energy expenditure, that are delivered to external customers 18.

According to the invention, part of the liquid phase 12 of the organic residue as well as the water 20 from the microalgae culture unit 14, still containing a portion of NPK nutrients, are supplied to a macrophyte or aquatic plants culture unit 22, in a greenhouse of the vegetable crop type.

The production 30 of carbon dioxide $CO_2$ from the units for methanization 6 and cogeneration 8 is spread to the units for microalgae culture 14 and macrophyte culture 22 to improve yields.

The macrophyte harvest 22 is crushed and then used for vermiculture 24 under greenhouses nearby, which also receives digestate sludge 36 from the methanization unit 6. The products from the vermiculture 24 yield a percolate 26 as well as vermiculture compost 28, which are supplied to external customers 64.

Hot water 32 produced by the units for methanization 6 and for cogeneration 8 is fed to the cultivation units 14, 22 and to the vermiculture 24 to enable the transformation processes.

In addition, the treatment and recycling facility can very advantageously include nearby timber operations, notably willow varieties with rapid growth, that use the compost produced by the vermiculture 24.

Figure 2:
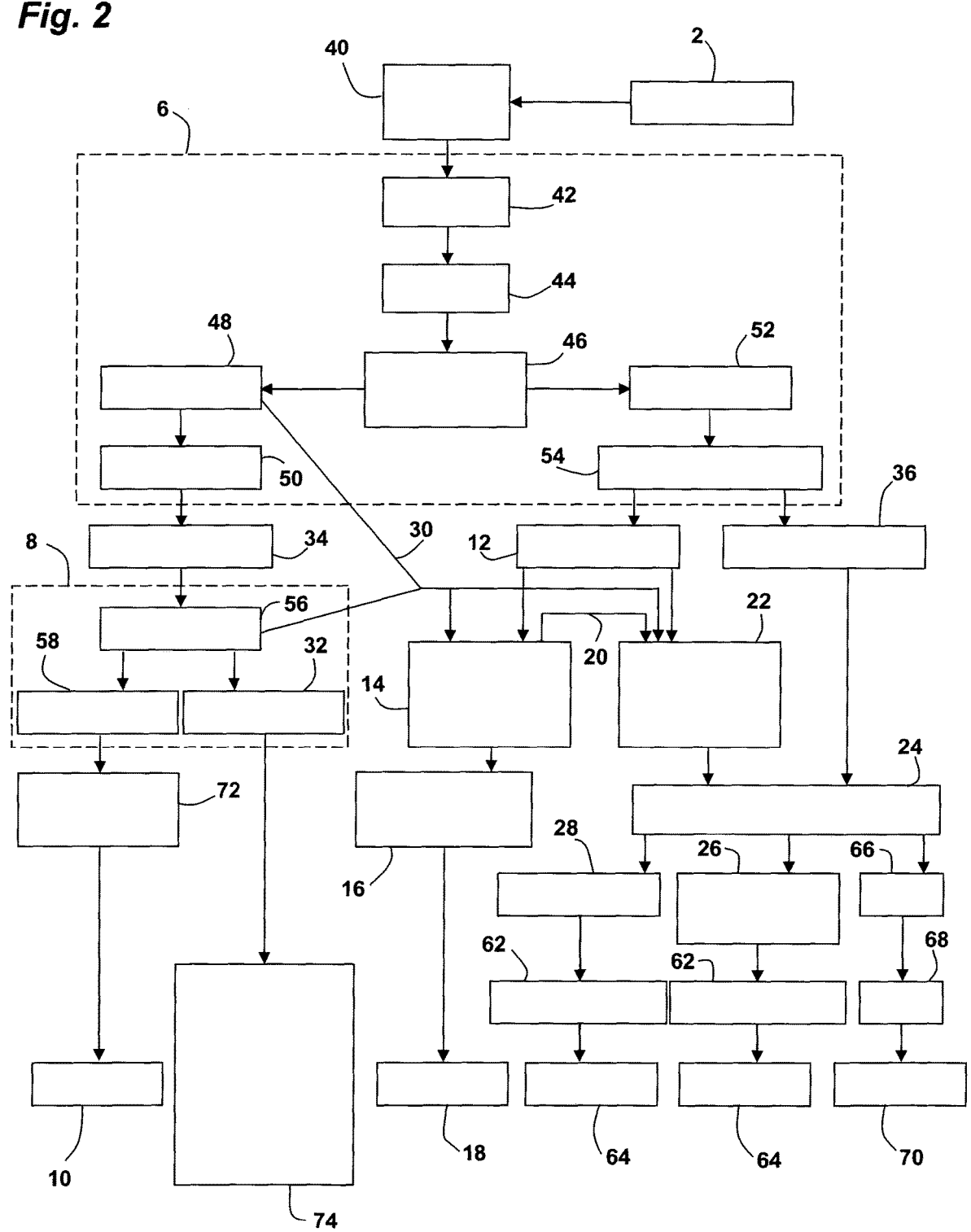
FIG. 2 is a graph showing the various steps of this facility, further comprising a timber operation.

FIG. 2 is a graph showing the various processes used in the treatment and recycling facility that perform a combination, wherein each of these processes uses proven techniques in installations in France or abroad.

The overall strategy of combining the different processes used aims to ensure optimum security of the decontamination process, in case of disruption of one of the biological processes, and to diversify the range of marketable output products, in order to ensure better stability of the company's revenues, especially in case of change in the price of products on the international markets.

For the methanization unit 6, effluents 40 from breeders 2 go through a receiving station 42 followed by storage means 44, before performing the methanization 46.

The methanization 46 is an anaerobic digestion that constitutes a natural process in the absence of oxygen, and which is found especially in marshes, rivers, as well as in the digestive system of some animals such as ruminants. Methanization, ensured through the action of bacteria, has the main effect of producing biogas 34 consisting of approximately 60% $CH_4$ methane and 40% carbon dioxide $CO_2$.

The methanization unit 6 comprises several reactors called digesters, producing raw biogas 48 that is processed by purification 50 to remove notably water vapor and hydrogen sulfide $H_2S$, in order to yield recoverable biogas 34, equivalent to natural gas but renewable.

The reactors also supply a stabilized organic residue called raw digestate 52. The raw digestate 52, comprising all the NPK nutrients present in slurry, but in a form more available to plants, goes through a separation system 54 including a decantation, filtration and hygienization, for supplying a liquid phase of the digestate 12 and a solid phase comprising digestate sludge 36.

The methanization process used is the mesophilic type, comprising a temperature between 32 to 40° C., which is less sensitive and more stable than other methods including tighter and higher temperature ranges. Thus, the process stability is privileged at the expense of higher productivity, in order to ensure uninterrupted pollution control and a constant supply of thermal energy for the proper development of the facility's cultures.

Moreover, this mesophilic process is better suited for regions with a temperate climate, since it avoids a greater energy consumption to reach higher temperatures.

The technology chosen for the digesters is that of the covered pool, which allows the management of large volumes with security guarantees and a reasonable construction cost. This technique has the advantage of ensuring proper integration into the landscape, avoiding the high silos typically used for wet methanization.

In particular, it is possible to economically implement semi-buried rectangular pools dug in clay soil and enhanced on the sides by the excavated soil, provided at the bottom with a waterproof membrane.

Advantageously, several pools are made connected to one another to achieve flexibility in the management of these pools for maintenance, with the possibility to quickly transfer effluent from one pool to the other without stopping the decontamination cycle, both in case of problems and for periodic checks. In this way, better environmental safety is achieved.

Advantageously, the pools are placed in greenhouses of the culture units for microalgae 14, macrophytes 22 or vermiculture 24, so as to provide additional thermal insulation of the surface of these pools to ensure proper operation of the anaerobic digestion, to limit the total floor area of the entire facility and reduce the visual impact on the landscape.

The upgraded biogas 34 is supplied to the cogeneration unit 8, comprising a cogenerator 56 having a motor driving an alternator supplying an electric power 58 enabling the different electricity needs of the treatment facility to be covered, with the surplus 72 being sold to the external electrical distribution network 10. For security reasons, a certain distance is designed between the cogeneration unit 8 and the methanization unit 6.

The methanization unit 6 and the cogeneration unit 8 produce heat in the form of a hot water flow 32, which is used throughout the year on the site 74 by heating the greenhouses for the culture of microalgae 14, of macrophytes 22 and of vermiculture 24. Heat is also used to maintain the temperature of the digesters of the methanization unit. It is possible thus to achieve processes operating at substantially constant temperatures throughout the year, which evens out seasonal phenomena.

The carbon dioxide 30 produced by the methanization unit 6 and the cogeneration unit 8 is used by being supplied to the cultures of microalgae 14 and of macrophytes 22, in order to accelerate the growth of photosynthetic biomass. The carbon dioxide 30 is captured in the flue gases of the cogenerator 56 to yield a gas containing about 13% of this dioxide which is injected into the photo-bioreactors.

The microalgae selected for the hydroponic culture of the microalgae culture unit 14 grow in transparent tubes called photo-bioreactor "PBR", receiving a liquid containing NPK nutrients from the liquid phase of the digestate 12 as well as the carbon dioxide 30 dissolved in this liquid, in order to synthesize its biomass.

Advantageously, the transparent tubes, made of polymethyl methacrylate (PMMA), have a diameter of about 100 mm and are superimposed to form row arrays arranged in parallel.

The water contained in the culture tubes is maintained at a temperature of 25° C. by the greenhouse effect and by a water/water heat exchanger fed by the hot water circuit 32.

The dosages of NPK nutrient inputs and of carbon dioxide, and the temperature settings, are controlled by automated systems. It is in particular possible to adapt the parameters to obtain specific growths rich in some elements that are sought depending on the applications, such as for the pharmaceutical, cosmetic or food markets. These parameters may be the setting in terms of NPK nutrients, the dosage of carbon dioxide, the temperature, the adjustment of the pH acidity, the dosage in specific micro-elements, the supply of carbonated solution, the control of the brightness and of the light spectrum, the water flow velocity and the gas saturation of this water.

The selected algae strains are endowed with a rapid growth, which can yield a doubling of the mass in one day, and are rich in oils and valuable elements. This gives very high yields per hectare, which can be a hundred times higher than yields of plants grown in soil. Harvesting the microalgae occurs by tangential filtration through a membrane.

The microalgae are processed in the concentration and packaging station 16 to be supplied in liquid phase in drums. A product is thus achieved that has limited volume and mass, which enables transport costs as well as their pollution impact to be reduced.

Concentrated microalgae are used in particular on the cosmetic market, with lipid extracts, protein extracts and so-called anti-aging molecules, in the pharmacy sector with omega 3/6, in the food market with human or animal nutritional supplements, in industry with bio-plastics and dyes, and in the energy sector with oil extractions to replace fossil fuels, or methanization of biomass.

In addition, microalgae culture can generate a production of oxygen or hydrogen with some microalgae strains, these gases then being recovered by exchangers at the PBR photo-bioreactors tubes.

The microalgae culture absorbs about 75% of NPK nutrients, with water emerging from the photo-bioreactor 20 being then delivered to the hydroponics macrophyte culture 22 in heated greenhouses for a next stage of supplementary refining of this water.

The macrophyte culture unit 22 advantageously uses a plant from the family *Eichhornia crassipes*, commonly called water hyacinth, cultivated above ground in pools heated to about 25° C. This aquatic plant of tropical origin requires greenhouse cultivation in temperate regions; its growth is one of the fastest in the plant kingdom.

This type of water plant has a good ability to extract NPK nutrients and heavy metals contained in the water and can achieve total purification of polluted water as well as a decrease in its volume by transpiration and significant evaporation.

The macrophyte culture 22 receives both the liquid phase 12 of the raw digestate 52, rich in NPK nutrients, and the water 20 from the microalgae culture 14 still containing a portion of nutrients to purify them. In particular, 1 hectare of water hyacinth culture can purify about 250 $m^3$ of water per day.

Moreover, this plant can be used as organic fertilizer, and its flower, leaves and roots can be used as animal feed.

Advantageously, the culture pools arranged in greenhouses, having a limited depth of about 30 cm and a width of about 2 m, form rows spaced by a runway for a machine to roll on it to automatically perform the harvesting. The macrophytes are easily collected by a dedicated automatic machine, as they are floating on water and do not require cutting or tearing like for plants having roots in the ground.

The macrophytes collected are then ground in a chopper and then mixed with the methanization sludge 36 before being spread on the earthworm culture 24 to be digested by providing an indispensable plant complement to the growth of earthworms.

Greenhouse cultivation helps maintain optimum development conditions all year round in terms of light, temperature and $CO_2$ levels. It is thus possible to ensure a continuity of the process regardless of the seasons and weather conditions. It is furthermore possible to inject under controlled atmosphere the carbon dioxide from the biogas and cogeneration, in order to accelerate the growth of the plant. *Eichhornia crassipes*, like all photosynthetic organisms, in fact needs $CO_2$ for growth.

It will be noted that macrophytes that can purify highly charged waters have a biomass production ratio that is amongst the highest for air plants.

Filtration by the culture of earthworms 24 consists in raising earthworms in compost forming an organic support watered by a liquid loaded with organic material, to perform a biological process which helps digestion of these materials, while combining in a simple way a biological indication of the stability of the environment and of the smooth running of the purification process.

Earthworms breathe through contact with water from their environment, so it is important to keep a percentage of moisture of the medium in excess of 80%. In particular, the methanization sludge 36 concentrated to 15% of dry matter make it possible to keep an optimum moisture of the compost. Advantageously, earthworms of the "California" type, which are well suited for this function, will be used.

Naturally, earthworms let out of their digestive tract a liquid called percolate or leachate 26, loaded with bacteria, which will serve as a soil enhancer. The compost is prepared in the form of strips in greenhouses of the vegetable crop type, directly on the floor on a waterproof tarpaulin to ensure the recovery of the percolate 26 through drains.

The optimum temperature for the culture of earthworms 24, which is 20° C., is provided by circulation of hot water under the compost layer.

The growth of the population of earthworms is ensured by the supply of plant material from the macrophyte culture 22, and methanization sludge 36. Once the compost has matured, the earthworms are removed to seed into neighboring lines.

The resulting compost 28 is removed and packaged 62, the percolate 26 is also packaged 62, these products being used with significant economic value to users running organic cultivation systems 64.

Earthworms consume the solid phases of the methanization sludge 36. The percolate, soaked to 100% humidity, and the produced compost, soaked to approximately 85% moisture, absorb some of the water produced by the facility, in addition to water dissipated through evaporation and transpiration by the macrophyte culture.

By sizing the various elements of the facility, one can thus achieve a complete consumption of the sludge as well as of the water produced by this facility, which avoids them being discarded, spread or discharged following plans subject to standards and to authorizations in order to avoid pollution.

It will be noted that excess intake of NPK nutrients in the soil can destroy the bacterial flora necessary for achieving an absorption of these elements by plants and can make the soil barren. Plant growth is then impossible. The use of the percolate 26 or of the compost 28 from earthworms makes it possible to give the soil the bacteria coming from the digestive system of the earthworm, which are ionic transmitters that restore the ability of plants to absorb NPK nutrients present in the earth.

The last unit of the treatment and recycling facility according to the invention, used optionally as a complement, will advantageously comprise an intensive culture of willow in short rotation 66, also known as short rotation coppice "SRC", which receives compost from the earthworm culture 24. Its main role is to capture $CO_2$ carbon dioxide, but this culture also plays a role in the natural evaporation of liquid discharges already filtered by the preceding processing units, in order to limit the release of water back into the natural environment by the hydraulic surface network.

For a facility processing between 110,000 and 146,000 tons of pig manure per year, or an average processing of 350 tons per day, with an installed capacity of 400 tons per day, estimates yield a production of microalgae used by the food, pharmaceutical and cosmetics industry of 2,500 tons of dry matter per year, an earthworm compost production of 21,000 tons per year, and a biological growth accelerator that is ready-to-use in liquid form provided by the earthworm percolate of 9,000 tons per year. The cultivation area of water hyacinth is planned to be 5 ha.

This facility can absorb through natural evaporation or by exporting through value-enhanced products the full 350 tons per day of liquid entering the process.

It allows in particular farmland of low agricultural value to be used, such as the moors or marginal lands, thanks to the soil-less cultivation system.

It goes without saying that the invention is not limited to the preferred embodiments described above. It encompasses on the contrary all possible embodiments, provided that these do not fall outside the scope defined by the appended claims which define the scope of the present invention.

What is claimed is:

1. A facility for treating and recycling animal waste, comprising an effluent methanization unit capable of producing and treating biogas obtained, a cogeneration unit providing electricity and heat from the biogas, a hydroponic microalgae culture unit in photo-bioreactors fed by part of the liquid phase of the raw digestate produced by methanization in the effluent methanization unit, and a system of separation capable of supplying a digestate liquid phase and a solid phase comprising digestate sludge, characterized in that it further comprises a macrophyte culture unit fed by the water emerging from the microalgae culture unit and by another part of the liquid phase of the raw digestate produced by the methanization in the effluent methanization unit, and a vermiculture unit fed by macrophytes harvested from the macrophyte culture unit, ground in a chopper unit and mixed with the sludge constituting the solid phase of the raw digestate from methanization.

2. The facility according to claim 1, characterized in that at least one digester is a pool covered by greenhouses of the microalgae, macrophyte or vermiculture cultures.

3. The facility according to claim 1, characterized in that the macrophyte culture uses a plant of the family *Eichhornia crassipes*.

4. The facility according to claim 1, characterized in that the harvested macrophytes are grown in greenhouses, above ground in culture pools heated to about 25° C.

5. The facility according to claim 4, characterized in that the culture pools have a depth of about 30 cm and a width of about 2m, and form rows separated by a runway for a machine to roll on.

6. The facility according to claim 1, characterized in that earthworms of the vermiculture are Californian.

7. The facility according to claim 1, characterized in that compost from the vermiculture has a humidity percentage of a medium that is greater than 80%.

8. The facility according to claim 1, characterized in that the vermiculture includes means for recovering percolate.

9. The facility according to claim 8, characterized in that compost from the vermiculture is placed in greenhouses directly on the ground on a waterproof tarpaulin, with drains being installed for recovering the percolate.

10. The facility according to claim 1, characterized in that the vermiculture is heated to about 20° C. by a hot water circulation coming from at least one digester and cogenerator.

11. The facility according to claim 1, further comprising a timber operation enriched by compost from the vermiculture.

12. The facility according to claim 11, characterized in that the timber operation uses willow in short rotation for pruning cycles.

13. Method for treating and recycling animal waste, characterized in that it comprises the following steps: a methanization of the effluents comprising a processing of biogas obtained, a cogeneration supplying electricity and heat from the biogas, a hydroponic microalgae culture in photo-bioreactors fed by part of the liquid phase of the raw digestate produced by the methanization, a separation supplying a digestate liquid phase and a solid phase comprising digestate sludge, a macrophyte culture fed by the water emerging from the microalgae culture unit and by another part of the liquid phase of the raw digestate produced by the methanization, and a vermiculture fed by macrophytes harvested from the macrophyte culture, and by the sludge constituting the solid phase of the raw digestate from methanization.

14. The facility according to claim 1, characterized in that carbon dioxide gas CO2 contained in the biogas is recovered and flows to the microalgae culture and to the macrophyte culture.

15. An apparatus for treating and recycling animal waste, comprising:
 an effluent methanization unit;
 a cogeneration unit connected to receive biogas from the effluent methanization unit;
 a hydroponic microalgae culture unit connected to receive a first part of liquid phase of raw digestate from the effluent methanization unit;
 a macrophyte culture unit connected to receive a second part of the liquid phase of raw digestate from the effluent methanization unit and connected to receive water from the hydroponic microalgae culture unit; and
 a vermiculture unit connected to receive harvested macrophytes from the macrophyte culture unit and connected to receive digestate sludge from the effluent methanization unit.

16. A facility for treating and recycling animal waste, comprising:
 an effluent methanization unit configured to produce and treat biogas comprising methane and carbon dioxide and configured to produce raw digestate;
 a cogeneration unit configured to provide electricity and heat in the form of hot water from biogas, and configured to produce carbon dioxide;
 a system of separation configured to separate the raw digestate to a digestate liquid phase and a solid phase comprising digestate sludge; and
 a hydroponic unit for cultivating microalgae in photo-bioreactors configured to receive a part of the digestate liquid phase;
 wherein the facility further comprises:
  a macrophyte culture unit configured to receive water emerging from the hydroponic unit and by another part of the digestate liquid phase; and
  a vermiculture unit configured to receive macrophytes harvested from the macrophyte culture unit and the digestate sludge;
 wherein the hydroponic unit for cultivating microalgae and/or the macrophyte culture unit and/or the vermiculture unit are configured to receive heat from the methanization unit or cogeneration unit;
 wherein the hydroponic unit for cultivating microalgae and/or the macrophyte culture unit are configured to receive carbon dioxide from the methanization unit or cogeneration unit.

* * * * *